United States Patent
Alshammari et al.

(10) Patent No.: US 8,536,374 B2
(45) Date of Patent: Sep. 17, 2013

(54) METHOD FOR PREPARATION OF DICARBOXYLIC ACIDS FROM SATURATED HYDROCARBONS OR CYCLOALIPHATIC HYDROCARBONS BY CATALYTIC OXIDATION

(75) Inventors: Ahmad Alshammari, Riyadh (SA); Narayana Venkata Kalevaru, Hyderabad (IN); Angela Koeckritz, Berlin (DE); Andreas Martin, Berlin (DE)

(73) Assignee: King Abdulaziz City for Science and Technology, Riyadh (SA)

( * ) Notice: Subject to any disclaimer, the term of this patent is extended or adjusted under 35 U.S.C. 154(b) by 50 days.

(21) Appl. No.: 13/269,988

(22) Filed: Oct. 10, 2011

(65) Prior Publication Data

US 2012/0095258 A1    Apr. 19, 2012

(30) Foreign Application Priority Data

Oct. 15, 2010  (EP) .................................... 10187728

(51) Int. Cl.
*C07C 51/31* (2006.01)
*C07C 51/215* (2006.01)

(52) U.S. Cl.
USPC .......................................... 562/543; 562/549

(58) Field of Classification Search
CPC ...................................................... C07C 51/31
See application file for complete search history.

(56) References Cited

U.S. PATENT DOCUMENTS

| | | | |
|---|---|---|---|
| 3,390,174 A | 6/1968 | Schulz et al. | |
| 5,294,739 A | 3/1994 | Kraushaar-Czarnetzki et al. | |
| 6,235,932 B1 | 5/2001 | Mall et al. | |
| 6,392,093 B1 | 5/2002 | Saji et al. | |

FOREIGN PATENT DOCUMENTS

| | | |
|---|---|---|
| EP | 0519569 A2 | 12/1992 |
| EP | 0784045 B1 | 7/1997 |
| GB | 1304855 A | 1/1973 |
| WO | WO-0100555 A1 | 1/2001 |

OTHER PUBLICATIONS

White et al, Basic Energy Sciences Advisory Committee Subpanel Workshop Report, Opportunities for Catalysis in the 21st Century, 2002, pp. 1-47.*

* cited by examiner

*Primary Examiner* — Paul A Zucker
(74) *Attorney, Agent, or Firm* — Andrew M. Calderon; Roberts Mlotkowski Safran & Cole, P.C.

(57) ABSTRACT

The present invention relates to a method for preparing dicarboxylic acids from saturated and cycloaliphatic hydrocarbons by oxidation at a reaction temperature comprised in the range of 25 to 300° C. in an autoclave using a solid heterogeneous catalyst. More particularly, the method of the invention relates to a method for preparing adipic acid (AA) from cyclohexane (CH) by selective oxidation.

27 Claims, No Drawings

US 8,536,374 B2

METHOD FOR PREPARATION OF DICARBOXYLIC ACIDS FROM SATURATED HYDROCARBONS OR CYCLOALIPHATIC HYDROCARBONS BY CATALYTIC OXIDATION

The present application claims priority under 35 U.S.C. §119 to application No. EP 10187728, filed on Oct. 15, 2010, the contents of which are incorporated in their entirety by reference herein.

FIELD OF THE INVENTION

In a first aspect, the present invention relates to a method for preparing dicarboxylic acids from saturated hydrocarbons or cycloaliphatic hydrocarbons by catalytic oxidation. The reaction is preferably carried out in an autoclave. Subject matter of the invention is further the preparation of a noble metal catalyst supported on a catalyst carrier, especially of a supported nano-gold catalyst. In a further aspect, the present invention relates to a method for preparing adipic acid (AA) from cyclohexane (CH) with an oxidising agent and using a heterogeneous catalyst.

BACKGROUND OF THE INVENTION AND PRIOR ART REFERENCES

The selective oxidation of cycloaliphatic hydrocarbons to dicarboxylic acids, in particular, cyclohexane to adipic acid is indeed an industrially important reaction. The target product, adipic acid, is an extremely important commodity chemical for the manufacture of polyamides (e.g. nylon 6,6), polyurethanes, polyesters, plasticizers (e.g. PVC), and for the production of intermediates for pharmaceuticals, insecticides etc. Furthermore, it is also used in medicine and food industry for different applications.

The current production process of AA on a commercial scale involves two-steps. The first step deals with the oxidation of cyclohexane to produce mainly a mixture of cyclohexanone and cyclohexanol, the so-called KA-oil process (KA=Ketone and Alcohol) at around 150° C. and at 10-20 bar of air using a cobalt or a manganese catalyst. In the second step, the resulting mixture of KA is subsequently converted into AA using nitric acid as an oxidant. The majority of AA available in the market is made through KA-oil process according to the steps mentioned above. The main drawback of this method is the needed very low conversion levels of CH(X=≦5%) to reach high KA selectivity (70-85%). This requires large recycling (>90%) of un-reacted CH and hence incurs some additional costs. Another disadvantage of this method is concerning environmental issues. For instance, the usage of nitric acid as an oxidant in the second step of this process undeniably generates certain amounts of $NO_x$ in the product stream, which in turn needs some efforts to remove $NO_x$ from exhaust gases and not to liberate it to the atmosphere. Therefore, there is a need to look for other alternatives or develop new and attractive routes that can avoid usage of environmental unfriendly reagents. Various possible routes that can be used for producing adipic acid are known from the literature. Although different opportunities exist, the direct oxidation of cyclohexane to adipic acid in one step using molecular oxygen as an oxidant is indeed an effective and economic approach, which is also the main task of the present invention.

Even though some of the above processes are being practiced commercially, some process options for AA production in absence of $HNO_3$ usage were also proposed by various research groups in different patents (e.g. GB 1304 855 (1973) and U.S. Pat. No. 3,390,174 (1968)). Nevertheless, these approaches gave only poor selectivities (S=30-50%) of desired products such as KA and/or adipic acid. An additional problem of most of these processes is usage of soluble homogeneous catalysts, which pose difficulty of separation after the reaction.

F. T. Starzyk et al. (Stud. Surf. Sci. Catal. 84 (1994) 1419) have applied "iron phthalocyanine encapsulated in Y-zeolite" as a solid catalyst. However, this process strongly suffers from much longer induction periods, i.e. the catalyst requires about 300 h to reach CH conversion of ca. 35% and needs 600 h to get higher amounts of adipic acid in the product stream, which makes the process commercially unattractive.

EP 519 569 (1992) report the use of Cobalt substituted ALPO-5 catalyst for the synthesis of AA by the oxidation of CH in acetic acid as a solvent. However, in this process, the possibility of formation of stable cyclohexylacetate as an additional by-product can not be ruled out because of the reaction between intermediate cyclohexanol and acetic acid. The formation of such unwanted by-product involves some additional separation costs. Furthermore, acetic acid is also corrosive solvent and hence difficulty of handling it in larger amounts on commercial scale and also special equipment is required for long-term operations dealing with acetic acid.

U.S. Pat. No. 6,392,093 (2002) discloses the use of a solid organotransition metal complex (e.g. encapsulated salen or substituted salen metal complex) for the oxidation of cyclohexane to adipic acid. Conversion levels of CH≦20% and the yield of AA below 10% are achieved. Another patent, EP 0784 045 B1 (2000) reported the use of metal incorporated tetra deca halo (nitro) phthalocyanine catalysts, where the metal=Co, Cu, Cr, Mn. They claimed the conversion of CH in the range from 6-15%, yield of AA=3-10% and the sum of yields of both cyclohexanone and cyclohexanol together 3-6%. In addition, WO 01/00555 A1 (2001) and U.S. Pat. No. 6,235,932 B1 (2001) describe a process for converting CH into AA employing the salts of Co or Co—Fe as catalysts mostly in acetate form. Although this patent claims high conversion of CH (13-55%) with good selectivity of AA (55-70%), these catalysts suffer from other problems such as an additional activation step prior to their use in the reactor, easy solubility of acetate salts (leaching) and the probability of formation of additional by-products (e.g. cyclohexyl acetate) can not be ruled out due to presence of acetates in reacting mixture. Moreover, such extra activation was done in an additional apparatus by bubbling oxygen through a solution of cobaltous-iron acetate in acetic acid at 90 to 130° C. in presence of methyl ethyl ketone or acetaldehyde etc. as promoters, which makes the approach complex.

Furthermore, efforts were also made by various researchers to use gold-based catalysts for the direct oxidation of CH to AA, but to the best of our knowledge all such attempts went unsuccessful until now. For instance, various gold catalysts such as Au/graphite (Y. J. Xu, P. Landon, D. Enache, A. F. Carley, M. W. Roberts, G. J. Hutchings, Catal. Lett. 101 (2005) 175.), Au/MCM-41 (G. Lu, R. Zhao, G. Qian, Y. Qi, X. Wang, J. Suo, Catal. Lett. 97 (2004) 115.), Au/SBA-15 (G. Lu, D. Ji, G. Qian, Y. Qi, X. Wang, J. Suo, Appl. Catal. A: Gen. 280 (2005) 175.), $Au/CeO_2$ (A. Corma, J. Lopez Nieto, U.S. Pat. No. 7,166,751 (2007)), $Au/SiO_2$ (L. X. Xu, C. H. He, M. Q. Zhu, K. J. Wu, Y. L. Xu, Catal. Lett. 118 (2007) 248.) and $Au/Al_2O_3$ (L. X. Xu, C. H. He, M. Q. Zhu, K. J. Wu, S. Fang, Catal. Lett. 114 (2002) 202.) were applied for the said reaction, which gave only cyclohexanol and cyclohexanone as major products without any adipic acid in the product stream. Using such catalyst systems, the conversion of CH was varied in the range from 6 to 20% but again almost no adipic acid formation was reported. However, the selectivity of both cyclohexanol and cyclohexanone products together were found to be in the range of 17 to 90%. Very recently, Hereijgers and Weckhuysen tried to use supported Au catalysts using various catalyst carries for the direct oxidation of CH to AA (B. P. C. Hereijgers, B. M. Weckhuysen, J. Catal. 270 (2010) 16.). However, these efforts again gave mainly cyclohexanone and cyclohexanol as main products (sum of selectivity of these two products are ca. 70% at a conversion of CH above 5%.

The object of the present invention is therefore to find effective and potential catalyst compositions for a direct method for producing dicarboxylic acids in a single step. The invention also aims to supply an easy method for preparing the catalyst and its use in the said oxidation reaction.

Especially it is an object of the present invention to provide a direct method for the preparation of adipic acid from cyclohexane in a single step.

DESCRIPTION OF THE INVENTION

The main focus of the present invention relates to a method for preparing dicarboxylic acids by the selective oxidation of saturated hydrocarbons and/or cycloaliphatic hydrocarbons (cycloalkanes) at a reaction temperature comprised in the range of 25 to 300° C., preferably in the range of 50 to 250° C. using a heterogeneous catalyst in an autoclave.

The term "hydrocarbon" moiety as used herein means a straight chain or branched-chain saturated hydrocarbon moiety is selected from the group of alkanes having from 1 to 10 carbon atoms in the chain.

According to the method of the invention, the starting compounds are especially "cycloaliphatic hydrocarbons". The term "cycloaliphatic hydrocarbons" refers to cyclic derivates, which bear a cyclic ring having from 3 to 8 carbon atoms in the ring. The cyclic ring may also contain as a side chain one or more alkyl moieties. Examples of such alkyl moieties include but are not limited to methyl, ethyl, diethyl, n-propyl, isopropyl, di-isopropyl, acetyl, n-butyl, isobutyl, sec-butyl, tert-butyl, pentyl, hexyl, and the like.

The cycloaliphatic hydrocarbon compounds can also contain one or more substituents such as halogen group, hydroxyl group, alkoxy group, amino group, nitro group, cyano group, phenyl group and the like. Preferred examples of cycloaliphatic hydrocarbons include cyclopropane, cyclobutane, cyclopentane, cyclohexane, alkyl substituted cyclohexanes and the like. These compounds may be used singly or in combination.

In a more preferred embodiment, the said cycloaliphatic hydrocarbon compound is cyclohexane. Thus, the invention relates to a method for preparing adipic acid by the oxidation of cyclohexane using supported nano-gold catalyst.

"Oxidation" refers to the process wherein the selected hydrocarbon moiety is converted into oxidized products, which comprise alcohols, aldehydes, ketones and carboxylic acids in one step using a catalyst and in presence of oxygen (air).

The method according to the invention is carried out under suitable reaction conditions. In a preferred embodiment, the method of the present invention is carried out at a reaction temperature comprised in the range of 25 to 300° C. The reaction pressure may be atmospheric, sub-atmospheric or super-atmospheric. Preferably the pressure is in the range from atmospheric to 100 bars.

A solid heterogeneous catalyst is used which is a noble metal catalyst supported on a catalyst carrier with the formula M/support, wherein M is chosen from the group consisting of Au, Pd, Pt, Ru and/or Ag and the support is selected from the group consisting of oxides of titania, alumina, silica, ceria, beryllia, magnesia, calcium, zirconia and tungsten as well as of silicon carbide, asbestos, diatomaceous earth, aluminosilicates and zeolites.

In a preferred embodiment of the present invention, the oxidation of cyclohexane is carried out using oxygen as an oxidizing agent. However, the source of oxygen can be pure oxygen gas, air, or a mixture of oxygen and an inert gas as diluent. The diluents can be selected from the group consisting of nitrogen, helium, argon, neon and the like.

In a preferred embodiment the catalyst is a nano-gold supported catalyst wherein M is Au in the range from 0.1 to 30 wt %, preferably in the range from 0.2 to 10 wt %.

The catalyst support is especially selected from the group consisting of $TiO_2$, MgO, CaO, $ZrO_2$ and $WO_3$, preferably $TiO_2$.

In another embodiment of the present invention, the solvent used in the reaction may be selected from the group consisting of water, acetonitrile, benzene and any other organic solvent, which is inert under the conditions applied.

The method according to the present invention by the direct oxidation can be carried out in batch process using the catalysts in a stainless steel autoclave under the conditions mentioned above. However, the process according to the present invention can also be carried out in semi-continuous (e.g. cascade method) as well as in continuous process.

The invention provides a method wherein the stirring speed of reaction mixture is varied in the range of 200 to 4000 rpm, preferably in the range of 300 to 2000 rpm.

The method according to the present invention can be carried out in a stainless steel Parr autoclave (vol: 100 ml) and heated electrically. $O_2$ gas supplied is commercially available gas from compressed gas cylinder. A liquid feed (i.e. CH, solvent, and an activator, i.e. TBHP) is placed in an autoclave in desired amounts. In a typical experiment, 400 milligrams of catalyst is added into the mixture, desired stirring speed of the reaction mixture is set and then the pressure of $O_2$ is also set to an appropriate level. Then the temperature is raised to the desired level and the reaction is performed. At the end of the reaction, the solid catalyst was separated by centrifugation. The product stream is analysed by gas chromatography equipped with FID. Some selected experiments at ambient pressure are also performed using a glass reactor in a similar way as described above.

The used catalyst is produced by:
preparation of an aqueous colloidal metal solution from a suitable precursors reduction of the metal solution using an aqueous solution containing appropriate auxiliary agents, selected from citric acid, tannic acid, tartaric acid, oxalic acid and the like,
impregnation of above colloidal solution onto a catalyst support followed by evaporation of excess solvent, preferably on a hot plate,
drying, preferably in an oven, and calcination under suitable conditions/atmosphere.

The calcining step is performed at a temperature in the range of 200 to 600° C. for a period of 2 to 50 hours, under a calcining atmosphere.

In particular, the present invention relates to a method for the preparation of AA by the one-pot oxidation of cyclohexane, which comprises reacting mixture of cyclohexane with $O_2$ (air) in presence of a solid heterogeneous catalyst (Scheme 1). More particularly, the said reaction is carried out at a reaction temperature comprised in the range of 50 to 250° C., more preferred at a temperature of more than 120° C., using a supported noble metal catalyst in an autoclave.

Scheme 1. Catalytic oxidation of cyclohexane using a heterogeneous catalyst

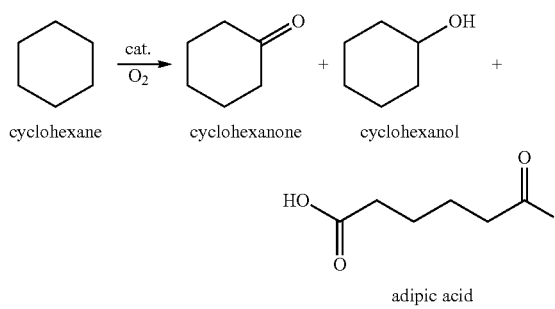

cyclohexane    cyclohexanone    cyclohexanol adipic acid

The catalysts, suitable for use in the above-described method, comprise a noble metal (M) supported on a suitable carrier, wherein the supported catalyst M is chosen from the group essentially comprising Au, Pd, Pt, Ru and/or Ag. The support is especially selected from the group consisting of $TiO_2$, MgO, CaO, $ZrO_2$, $WO_3$, diatomaceous earth, aluminosilicates or molecular sieves in the form of zeolites and the like.

According to the invention, $O_2$ (air) is supplied to an autoclave comprising preferably a supported nano-gold catalyst. The liquid feed [in particular CH and solvent (e.g. acetonitrile) as well as for example optional an activator as tert-butyl hydroperoxide (TBHP)] are mixed. Furthermore, the invention provides a method wherein the molar concentration of CH is preferably in the range from 1 to 30%, more preferably in the range from 2 to 20%. The mole ratio of solvent to CH is preferably in the range of 1 to 30, more preferred 4 to 20. The mole ratio of CH to TBHP is preferably in the range of 5 to 100, more preferred 10 to 60. The pressure of $O_2$ is in the range from atmospheric to 100 bar, preferably less than 50 bar. In particular, the $Au/TiO_2$ catalyst showed good potentiality and exhibits reasonably high conversion of CH (>25%) with good selectivity of AA. Thus, an acceptable yield of AA (ca. 8%) was successfully achieved. Therefore, in a particularly preferred embodiment, the invention relates to a method, wherein said catalyst is an $Au/TiO_2$ catalyst.

In contrast to most other known catalysts, which comprise multi-component and more complex catalyst compositions consisting of two or more promoters with them, the used catalyst of the present invention comprises only one metallic component supported on an oxide carrier and represents a very simple system exhibiting good performance.

In another embodiment, the invention provides a method for preparing the catalyst, comprising the steps of:
  preparation of colloidal gold solution from a suitable precursor
  reduction of the above solution using aqueous solution of tannic acid and sodium citrate
  impregnation of above colloidal solution on to the powdered catalyst support followed by evaporation of excess solvent on a hot plate
  oven drying and calcination under suitable conditions/atmosphere This novel preparation method allows providing an active and selective catalyst. This simple method of preparation also allows obtaining a catalyst with good performance.

A preferred precursor of the colloidal gold solution is $HAuCl_4$. The preparation procedure of the catalyst is detailed described in Example 1. In the first step, colloidal gold (where the Au is dispersed well in a liquid with the smallest possible size of Au), and then the colloidal solution is further impregnated onto the support (e.g. $TiO_2$). This method gave the smallest Au particles and hence superior performance as well. For the support $TiO_2$ for example a precursor in gel form is used which provides a $TiO_2$ carrier having an extremely high surface area (>300 $m^2/g$). In addition, the $TiO_2$ can be prepared from -sulphate precursor and hence some residues of acidic sulphates still retain in the support after final step of preparation. In difference known $TiO_2$ carriers show a surface area of only 55 $m^2/g$.

Then, the resultant solid catalyst is heated in a calcining atmosphere at a temperature in the range of 200° C. to 600° C., preferably in the range of 250° C. to 450° C., for a period of 2 to 50 hours, preferably in the range of 3 to 20 hours. The calcination can be done in different atmospheres, which include inert gas ($N_2$, He or Ar), air and reducing gas ($H_2$, CO); preferably air is used at a flow rate of 2-20 l/h, more preferably 3-10 l/h.

The preparation of the present catalyst also involves the usage of various sources of reducing agents. These reducing compounds may include citric acid, sodium citrate, ascorbic acid, sodium thiocyanate, sodium borohydride, tannic acid, tartaric acid, oxalic acid, salts of the same or the like. In addition, some auxiliary agents can also be used.

The invention provides CH conversion of over 25% with AA selectivity of 26% and ca. 70% selectivity of cyclohexanone and cyclohexanol together.

The present invention is illustrated in greater detail with reference to the following examples, but it is understood that the present invention is not deemed to be limited thereto. Example 1 illustrates the preparation of different supported nano-gold catalysts according to the invention. Example 2 describes the catalytic testing procedure. Example 3 presents the results of blank test in absence of catalyst. Example 4 shows the influence of various supports on the catalytic performance. Examples 5 to 10 refer to the influence of various reaction parameters on the catalytic performance of the best 1 wt % $Au/TiO_2$ catalyst. In the following examples, the conversion, yield and selectivity based on CH are illustrated:

Conversion(%)=$A/B$×100 where A is the number of moles reacted CH, and
B is the number of moles of CH fed to the reaction zone.

Yield(%)=$C/D$×100 where C is the number of moles AA obtained, and
D is the number of moles of CH fed to the reaction zone.

Selectivity(%)=$E/F$×100 where E is the number of moles AA obtained, and
F is the number of moles of reacted CH.

EXAMPLES

Example 1

Example 1 illustrates the preparation of supported nano-gold catalysts using various oxide supports according to the procedure described below.
Preparation of Supported Nano-Gold Catalysts
The preparation of the catalysts involves two steps such as the preparation of colloidal gold nanoparticles (AuNPs) solution using suitable reducing/auxiliary agents in the first step and its further impregnation onto a catalyst carrier in the second step. Interestingly this preparation showed good catalytic results compared to the prior art particularly on the gold catalysts. More details of this preparation method are described below:

Step 1: The first step involves the preparation of colloidal gold nanoparticles by the reduction of $HAuCl_4$ (0.06 g) using an aqueous solution containing 1% tannic acid, 1% sodium citrate solution and $K_2CO_3$ (0.1 g) at 60° C. To be brief, appropriate amounts of $HAuCl_4$ solution was prepared first and heated it to 60° C. in a beaker. Then, in a second beaker, required amount of reducing agent (e.g. sodium citrate/tannic acid) solution was prepared and it was also heated to 60° C. Afterwards, the solution of reductant was added to the $HAuCl_4$ solution under stirring until the reduction process of $Au^{+3}$ to $Au^0$ at a temperature of 60° C. was completed and as a result the formation of colloidal gold nanoparticles was observed. The formation of AuNPs was also indicated by the color of the resulting solution. After preparation of such colloidal gold nanoparticles, they were further impregnated onto a support using the procedure described below in the second step.

Step 2: In this step, the above-prepared colloidal gold solution (step 1) was further impregnated onto a catalyst support (e.g. $TiO_2$, 3 g) in powder form under stirring.

After impregnation (step 2), the slurry was vigorously stirred for another 2 hours at room temperature and then the excess solvent was removed on a rotary evaporator. The solid thus obtained was washed three times with water, and then it was oven dried at 120° C. for 16 h. The oven dried sample was finally calcined at 350° C. for 5 h in air.

Using the same procedure, four other supported nano-gold catalysts were also prepared in a similar way. The supports used were MgO, CaO, $ZrO_2$ and $Al_2O_3$. The gold content was always fixed constant at 1 wt %.

Example 2

Example 2 describes the procedure for catalytic testing of the present reaction carried out according to the invention.

Catalytic Tests

Activity tests were carried out under pressure using a Parr autoclave according to the procedure described below. In a typical experiment, the reaction mixture consisted of 0.4 g of supported gold catalyst, 5 ml of cyclohexane, 25 ml of acetonitrile as solvent, in general, and 0.1 g of tert-butyl hydroperoxide (TBHP), unless otherwise stated. These components were taken in an autoclave and flushed three times with $O_2$ before setting the initial reaction pressure of $O_2$ to 10 bar. Concerning the start-up procedure, it was performed with the $O_2$ line opened, and as $O_2$ was consumed, it was replaced from the cylinder, which maintains the overall pressure constant. The stirring speed of reaction mixture was set to 1500 rpm in general and the reaction was performed at 150° C. for 4 h unless otherwise stated. At the end of the reaction, the solid catalyst was separated by centrifugation. In addition, this reaction was also performed using a glass reactor consisting of 50 ml round-bottomed flask with a reflux-cooling condenser. The reaction conditions used for glass reactor tests were similar to the ones performed in the autoclave. Experiments were carried out using an oil bath at 150° C. for 4 h with continuous air bubbling through the reaction mixture (i.e. in the reactor). At the end of the reaction, the solid catalyst was separated by centrifugation. The identity of the reactions products for cyclohexane was confirmed by gas chromatography (Agilent 6890 N) fitted with a HP-5 column and a flame ionization detector (FID). In order to obtain the acids in the ester form, 500 µl of product sample was esterified with 400 µl of trimethylsulfonium hydroxide in the presence of internal standard (3-pentanone, 100 µl). After such derivatisation of acid to ester, 0.2 µl of this sample was injected off-line into GC and analyzed.

Example 3

A blank experiment was also executed by treating CH with oxygen and TBHP at 150° C. in the absence of catalyst. This blank test showed a conversion of CH of approximately 0.4% in the first 1 h. Subsequently, the conversion increased gradually to ca. 2% after 4 hours-on-stream. Comparing this result with that of a catalyzed reaction, it can be clearly noticed that the blank test in absence of catalyst has exhibited only a very low and negligible conversion and hence presence of a catalyst is essential and plays a key role on the performance.

Example 4

Example 4 describes the conversion of CH, selectivity of products during the catalytic oxidation reaction carried out according to the invention. The primary objective of this study is first to check the influence of support on the catalytic performance in the direction of finding suitable catalyst carrier and then to check the effect of various reaction conditions for identifying optimum reaction conditions taking the best support. With these objectives, the following catalysts were prepared according to the procedure given in Example 1 and tested according to Example 2 and the results are given in Table 1.

TABLE 1

Influence of support on the catalytic performance of various supported Au catalysts

| S. No. | Catalyst* | X-CH (%) | S-AA (%) | S-One (%) | S-OI (%) | S-others (%) |
|---|---|---|---|---|---|---|
| 1 | Au/MgO | 10.8 | 7.2 | 12.7 | 35.4 | 44.7 |
| 2 | Au/CaO | 15.2 | 4.5 | 11.3 | 34.9 | 49.3 |
| 3 | Au/ZrO$_2$ | 13.8 | 6.6 | 10.3 | 45.0 | 38.1 |
| 4 | Au/TiO$_2$ | 16.4 | 21.6 | 29.3 | 47.1 | 2.0 |
| 5 | Au/Al$_2$O$_3$ | 10.2 | 18.9 | 13.3 | 64.4 | 3.4 |

X-CH = conversion of cyclohexane;
S-AA = selectivity of adipic acid;
S-One = selectivity of cyclohexanone;
S-OI = selectivity of cyclohexanol;
S-Others = yields of glutaric acid, succinic acid, cyclohexylhydroperoxide, CO and $CO_2$,
Reaction conditions: 10 ml CH, 20 ml solvent (acetonitrile), 0.3 g catalyst, 0.1 g TBHP, p$O_2$ = 10 bar, t = 4 h, 1500 rpm, T = 130° C. (*Au loading is 1 wt %)

Among various catalysts tested, $TiO_2$ supported one exhibited better activity, selectivity and hence this catalyst was further investigated. The results obtained on such investigations are shown below one after the other.

Example 5

Example 5 demonstrates the effect of catalyst amount on the performance of 1 wt % Au/$TiO_2$ solid. This catalyst was prepared according to the procedure given in Example 1 and tested according to the procedure presented in Example 2. The results are shown below in Table 2. From the results, it appears that an amount of 400 mg is an optimum for better performance and hence this amount is used for further investigations.

TABLE 2

Variation of activity and selectivity of 1 wt %
Au/TiO$_2$ catalyst with varying amount of catalyst

| Catalyst wt. (mg) | X-CH (%) | S-AA (%) | S-One (%) | S-Ol (%) | S-Others (%) |
|---|---|---|---|---|---|
| 200 | 7.4 | 11.0 | 34.3 | 49.7 | 5.0 |
| 300 | 15.8 | 21.4 | 21.7 | 48.9 | 8.0 |
| 400 | 26.0 | 26.3 | 12.3 | 58.4 | 3.0 |
| 500 | 22.4 | 23.7 | 32.1 | 36.7 | 7.5 |

X-CH = conversion of cyclohexane; S-AA = selectivity of adipic acid; S-One = selectivity of cyclohexanone; S-Ol = selectivity of cyclohexanol; S-Others = yields of glutaric acid, succinic acid, cyclohexylhydroperoxide, CO and $CO_2$, Reaction conditions: 5 ml CH, 25 ml solvent (acetonitrile), 0.1 g TBHP, $pO_2$ = 10 bar, t = 4 h, 1500 rpm.

Example 6

Example 6 illustrates the time-on-stream behaviour of the 1 wt % Au/TiO$_2$ solid. This catalyst was prepared according the procedure given in Example 1 and tested according to the procedure presented in Example 2. The results are shown below in Table 3. It seems that the catalyst exhibited good performance at 4 h and hence this reaction time is further used.

TABLE 3

Variation of activity and selectivity of 1
wt % Au/TiO$_2$ catalyst with time-on-stream

| Time (h) | X-CH (%) | S-AA (%) | S-One (%) | S-Ol (%) | S-Others (%) |
|---|---|---|---|---|---|
| 0.5 | 2.0 | 0.7 | 25.7 | 49.6 | 24.0 |
| 1 | 11.8 | 4.2 | 27.6 | 49.1 | 19.1 |
| 3 | 16.6 | 21.4 | 29.4 | 46.9 | 2.3 |
| 4 | 26.0 | 26.3 | 12.3 | 58.4 | 3.0 |
| 6 | 21.4 | 24.6 | 19.9 | 45.5 | 10.0 |
| 8 | 22.2 | 23.3 | 19.2 | 43.1 | 14.4 |

X-CH = conversion of cyclohexane; S-AA = selectivity of adipic acid; S-One = selectivity of cyclohexanone; S-Ol = selectivity of cyclohexanol; S-Others = yields of glutaric acid, succinic acid, cyclohexylhydroperoxide, CO and $CO_2$, Reaction conditions: 5 ml CH, 25 ml solvent (acetonitrile), 0.4 g catalyst, 0.1 g TBHP, $pO_2$ = 10 bar, 1500 rpm, T = 150° C.

Example 7

Example 7 refers to the influence of reaction temperature on the catalytic performance of 1 wt % Au/TiO$_2$ catalyst. The catalyst was prepared according to the procedure given in Example 1 and tested according to Example 2. The catalytic results obtained are given below in Table 4.

TABLE 4

Effect of reaction temperature on the oxidation
of cyclohexane over 1 wt % Au/TiO$_2$ catalyst

| T (° C.) | X-CH (%) | S-AA (%) | S-One (%) | S-Ol (%) | S-Others (%) |
|---|---|---|---|---|---|
| 100 | 2.4 | 5.6 | 14.3 | 66.5 | 13.6 |
| 130 | 12.8 | 18.9 | 11.8 | 64.3 | 5.0 |
| 150 | 26.0 | 26.3 | 12.3 | 58.4 | 3.0 |
| 170 | 28.2 | 28.5 | 11.1 | 12.0 | 48.4 |

X-CH = conversion of cyclohexane; S-AA = selectivity of adipic acid; S-One = selectivity of cyclohexanone; S-Ol = selectivity of cyclohexanol; S-Others = yields of glutaric acid, succinic acid, cyclohexylhydroperoxide, CO and $CO_2$, Reaction conditions: 5 ml CH, 25 ml solvent (acetonitrile), 0.4 g catalyst, 0.1 g TBHP, $pO_2$ = 10 bar, t = 4 h, 1500 rpm.

From these results, it appears that a reaction temperature of 150° C. seems to be optimum for better selectivity of desired products at reasonably good conversion and hence this temperature is used in further investigations.

Example 8

After successful tests on the influence of temperature, the further studies are focussed on checking the performance of 1 wt % Au/TiO$_2$ solid with varying reaction conditions. Example 8 describes the effect of solvent/CH ratio on the catalytic performance of 1 wt % Au/TiO$_2$ catalyst. The catalyst was prepared according to the procedure given in Example 1 and tested according to Example 2 at 150° C. and the results are presented in Table 5.

TABLE 5

Effect of solvent to CH ratio (v/v) on the catalytic performance
of 1 wt % Au/TiO$_2$ catalyst in the oxidation of cyclohexane

| Solvent: CH (ratio) | X-CH (%) | S-AA (%) | S-One (%) | S-Ol (%) | S-Others (%) |
|---|---|---|---|---|---|
| 1.0 | 37.2 | 4.7 | 5.5 | 6.4 | 83.4 |
| 1.5 | 34.0 | 9.6 | 8.8 | 9.6 | 72.0 |
| 2.5 | 23.8 | 12.7 | 11.8 | 28.0 | 47.5 |
| 5.0 | 26.0 | 26.3 | 12.3 | 58.4 | 3.0 |

X-CH = conversion of cyclohexane; S-AA = selectivity of adipic acid; S-One = selectivity of cyclohexanone; S-Ol = selectivity of cyclohexanol; S-Others = yields of glutaric acid, succinic acid, cyclohexylhydroperoxide, CO and $CO_2$, Reaction conditions: 0.4 g catalyst, 0.1 g TBHP, $pO_2$ = 10 bar, t = 4 h, 1500 rpm, T = 150° C.

Example 9

Example 9 depicts the influence of reaction pressure on the catalytic performance of the 1 wt % Au/TiO$_2$ solid. This catalyst was prepared according to the procedure given in Example 1 and tested according to the procedure presented in Example 2. The results are shown below in Table 6.

TABLE 6

Effect of reaction pressure on the catalytic performance of
1 wt % Au/TiO$_2$ catalyst in the oxidation of cyclohexane

| P (bar) | X-CH (%) | S-AA (%) | S-One (%) | S-Ol (%) | S-Others (%) |
|---|---|---|---|---|---|
| 1 | 2.2 | 0.01 | 11.1 | 66.3 | 22.5 |
| 5 | 13.8 | 6.58 | 10.9 | 45.0 | 37.5 |
| 7 | 16.2 | 20.8 | 30.1 | 46.0 | 3.1 |
| 10 | 26.0 | 26.3 | 12.3 | 58.4 | 3.0 |

X-CH = conversion of cyclohexane; S-AA = selectivity of adipic acid; S-One = selectivity of cyclohexanone; S-Ol = selectivity of cyclohexanol; S-Others = yields of glutaric acid, succinic acid, cyclohexylhydroperoxide, CO and $CO_2$, Reaction conditions: 5 ml CH, 25 ml solvent (acetonitrile), 0.4 g catalyst, 0.1 g TBHP, t = 4 h, 1500 rpm, T = 150° C.

Example 10

Example 10 presents the influence of stirring speed on the catalytic performance of the 1 wt % Au/TiO$_2$ solid. This catalyst was prepared according to the procedure given in Example 1 and tested according to the procedure described in Example 2. The results are shown below in Table 7.

TABLE 7

Influence of stirring speed on the catalytic performance of
1 wt % Au/TiO$_2$ catalyst in the oxidation of cyclohexane

| Stirring speed (rpm) | X-CH (%) | S-AA (%) | S-One (%) | S-Ol (%) | S-Others (%) |
|---|---|---|---|---|---|
| 500 | 16 | 18.7 | 22.5 | 46.2 | 12.2 |
| 1000 | 21.8 | 23.9 | 19.0 | 43.6 | 13.5 |

TABLE 7-continued

Influence of stirring speed on the catalytic performance of 1 wt % Au/TiO$_2$ catalyst in the oxidation of cyclohexane

| Stirring speed (rpm) | X-CH (%) | S-AA (%) | S-One (%) | S-OI (%) | S-Others (%) |
|---|---|---|---|---|---|
| 1500 | 26 | 26.3 | 12.3 | 58.4 | 3.0 |
| 2000 | 27.1 | 27.7 | 12.7 | 54.5 | 5.1 |

X-CH = conversion of cyclohexane; S-AA = selectivity of adipic acid; S-One = selectivity of cyclohexanone; S-OI = selectivity of cyclohexanol; S-Others = yields of glutaric acid, succinic acid, cyclohexylhydroperoxide, CO and CO$_2$, Reaction conditions: 5 ml CH, 25 ml solvent (acetonitrile), 0.4 g catalyst, 0.1 g TBHP, pO$_2$ = 10 bar, t = 4 h, T = 150° C.

What is claimed:

1. A method for the preparation of dicarboxylic acids from saturated hydrocarbons or cycloaliphatic hydrocarbons by catalytic oxidation comprising: oxidizing a hydrocarbon selected from the group consisting of alkanes having 1 to 10 carbon atoms in the chain and cycloaliphatic hydrocarbons having from 3 to 8 carbon atoms in the ring with oxygen as an oxidizing agent at a reaction temperature in the range of 25 to 300° C. using a solid heterogeneous catalyst being a noble metal catalyst supported on a catalyst carrier with the formula M/support, wherein M is selected from the group consisting of Au, Pd, Pt, Ru and/or Ag and the support is selected from the group consisting of oxides of titania, alumina, silica, ceria, beryllia, magnesia, calcium, zirconia and tungsten, and silicon carbide, asbestos, diatomaceous earth, aluminosilicates and zeolites.

2. The method according to claim 1, wherein the catalyst is a nano-gold supported catalyst and M is Au in the range from 0.1 to 30 wt %, based on the total weight of the catalyst.

3. The method according to claim 1, wherein the catalyst support is selected from the group consisting of TiO$_2$, MgO, CaO, ZrO$_2$ and WO$_3$.

4. The method according to claim 1, wherein the oxidation reaction is carried out in the presence of water, one or more organic solvents or mixtures thereof.

5. The method according to claim 1, wherein the oxidation reaction is carried out in the presence of a catalyst promoter, and wherein the activator is selected from the group consisting of alkyl hydroperoxides, dialkyl peroxides (alkyl=C1 to C5) and mixtures thereof.

6. The method according to claim 1, wherein the oxidation reaction is conducted in one of a batch process, a semi-continuous and a continuous process.

7. The method according to claim 1, wherein the oxidation reaction is carried out at a pressure comprised in a range from 1 bar to 100 bar.

8. A method for the preparation of adipic acid from cyclohexane which is directly oxidized to adipic acid in presence of at least one solvent in an autoclave using solid heterogeneous Au/TiO$_2$ catalyst and optionally a catalyst activator characterized in that the oxidation reaction is carried out at a reaction temperature in the range of 25 to 300° C.

9. The method according to claim 1, wherein the cycloaliphatic hydrocarbon is cyclohexane in a solvent in with a molar concentration of cyclohexane of 1 to 30%.

10. The method according to claim 9, wherein the molar ratio of solvent to cyclohexane is 2 to 25.

11. The method according to claim 1, wherein the used catalyst is produced by:
preparation of an aqueous colloidal metal solution from a suitable precursors,
reduction of the metal solution using an aqueous solution containing appropriate auxiliary agents,
impregnation of the colloidal solution onto a catalyst support followed by evaporation of excess solvent, and
drying and calcination under suitable conditions/atmosphere.

12. The method according to claim 11, wherein the precursor of the colloidal metal solution is HAuCl$_4$.

13. The method according to claim 11, wherein the auxiliary agents are selected from citric acid, tannic acid, tartaric acid, and/or oxalic acid.

14. The method according to claim 11, wherein the calcining step is performed at a temperature in the range of 200 to 600° C. for a period of 2 to 50 hours, under a calcining atmosphere.

15. The method according to claim 2, wherein the Au in the catalyst is in the range of from 0.2 to 10 wt %, based on the total weight of the catalyst.

16. The method according to claim 3, wherein the catalyst support is TiO$_2$.

17. The method according to claim 4, wherein the oxidation reaction is carried out in at least one of water, methanol, butanol, acetone, acetonitrile and benzene.

18. The method according to claim 5, wherein the activator is tert-butyl hydroperoxide.

19. The method according to claim 6, wherein the oxidation reaction is a batch process conducted in an autoclave.

20. The method according to claim 7, wherein the oxidation reaction is carried out at a pressure of less than 50 bar.

21. The method according to claim 1, wherein the cycloaliphatic hydrocarbon is cyclohexane.

22. The method according to claim 11, wherein the drying is in an oven.

23. The method according to claim 11, wherein the evaporation of excess solvent is conducted on a hot plate.

24. The method according to claim 8, wherein the oxidation reaction is carried out in the presence of a catalyst promoter, and wherein the activator is selected from the group consisting of alkyl hydroperoxides, dialkyl peroxides (alkyl=C1 to C5) and mixtures thereof.

25. The method according to claim 8, wherein the oxidation reaction is carried out at a pressure in a range from 1 bar to 50 bar.

26. The method according to claim 8, wherein the oxidation reaction is carried out in at least one of water, methanol, butanol, acetone, acetonitrile and benzene.

27. The method according to claim 8, wherein the oxidation reaction is a batch process conducted in an autoclave.

* * * * *